United States Patent
VanderSchuit

(10) Patent No.: US 8,257,416 B2
(45) Date of Patent: Sep. 4, 2012

(54) THERAPEUTIC DEVICES AND METHODS FOR APPLYING THERAPY

(76) Inventor: Carl R. VanderSchuit, San Diego, CA (US)

( * ) Notice: Subject to any disclaimer, the term of this patent is extended or adjusted under 35 U.S.C. 154(b) by 1809 days.

(21) Appl. No.: 11/442,581

(22) Filed: May 26, 2006

(65) Prior Publication Data

US 2006/0235494 A1 Oct. 19, 2006

Related U.S. Application Data

(63) Continuation-in-part of application No. 10/786,995, filed on Feb. 25, 2004, now Pat. No. 7,052,167.

(51) Int. Cl.
*A61F 7/00* (2006.01)

(52) U.S. Cl. ........ 607/108; 607/104; 607/109; 607/110; 607/111; 607/112; 607/114; 607/88; 607/94; 606/2; 606/19

(58) Field of Classification Search .......... 607/104–112, 607/114
See application file for complete search history.

(56) References Cited

U.S. PATENT DOCUMENTS

| | | | |
|---|---|---|---|
| 2,347,915 A | 5/1944 | Landauer | |
| 3,976,049 A | 8/1976 | Yamashita et al. | |
| 4,243,041 A * | 1/1981 | Paul | 607/109 |
| 4,868,384 A | 9/1989 | Franken et al. | |
| 4,907,132 A | 3/1990 | Parker | |
| 5,018,450 A | 5/1991 | Smith | |
| 5,358,503 A | 10/1994 | Bertwell et al. | |
| 5,568,964 A | 10/1996 | Parker et al. | |
| 5,616,140 A | 4/1997 | Prescott | |
| 5,643,336 A * | 7/1997 | Lopez-Claros | 607/104 |
| 5,766,233 A | 6/1998 | Thiberg | |
| 5,800,490 A | 9/1998 | Patz et al. | |
| 5,957,960 A | 9/1999 | Chen et al. | |
| 6,125,636 A | 10/2000 | Taylor et al. | |
| 6,187,029 B1 | 2/2001 | Shapiro et al. | |
| 6,221,095 B1 | 4/2001 | Van Zuylen et al. | |
| 6,249,698 B1 | 6/2001 | Parris | |
| 6,286,974 B1 | 9/2001 | Rochel et al. | |
| 6,416,198 B1 | 7/2002 | Vanderschuit | |
| 6,454,789 B1 | 9/2002 | Chen et al. | |
| 6,471,716 B1 | 10/2002 | Pecukonis | |
| 6,874,909 B2 | 4/2005 | Vanderschuit | |
| 6,935,761 B2 | 8/2005 | Vanderschuit | |

(Continued)

FOREIGN PATENT DOCUMENTS

CH 662 931 11/1987

(Continued)

OTHER PUBLICATIONS

Website: Wound News: Wound Technology; LED Technology Helps Wound Patients, by Adrian Brune for Wounds 1, dated Jul. 23, 2003, 2 pages, http://www.wounds1.com/news/tech.cfm/0.

(Continued)

*Primary Examiner* — Aaron Roane

(57) ABSTRACT

According to various aspects, exemplary embodiments are provided of therapeutic devices and methods for applying therapy. In one exemplary embodiment, a therapeutic device generally includes one or more light sources for emitting therapeutic light. In some embodiments, the therapeutic device can also include means for applying hot therapy and/or cold therapy to a user's body when the therapeutic device is applied to the user's body. As other examples, various embodiments of therapeutic devices can include massagers and/or adhesive bandage strips for attaching the lighted therapeutic device to the user's body.

5 Claims, 4 Drawing Sheets

U.S. PATENT DOCUMENTS

| | | |
|---|---|---|
| 6,955,450 B2 | 10/2005 | Johnson |
| 7,052,154 B2 | 5/2006 | Vanderschuit |
| 2001/0052153 A1 | 12/2001 | Schwartz et al. |
| 2003/0026088 A1 | 2/2003 | Vanderschuit |
| 2003/0056281 A1 | 3/2003 | Hasegawa |
| 2004/0039428 A1 | 2/2004 | Williams et al. |
| 2004/0093042 A1 | 5/2004 | Altshuler et al. |
| 2004/0147984 A1 | 7/2004 | Altshuler et al. |
| 2004/0249423 A1 | 12/2004 | Savage |
| 2004/0260365 A1 | 12/2004 | Groseth et al. |
| 2004/0264187 A1 | 12/2004 | Vanderschuit |

FOREIGN PATENT DOCUMENTS

| | | |
|---|---|---|
| DE | 299 18 185 | 1/2000 |
| GB | 2 392 973 | 3/2004 |
| WO | WO 93 18358 | 9/1993 |

OTHER PUBLICATIONS

Marshall Space Flight Center News Release 00-336 (Dec. 18, 2000): NASA Space Technology Shines Light on Healing, NASA News, dated Dec. 3, 2003, 4 pages, http://www1.msfc.nasa.gov/NEWS-ROOM/news/releases/2000/00-336.htm-l. cited by other.

United Kingdom Combined Search and Examination Report dated Jan. 6, 2004; Application No. GB0326549.3; 4 pages.

Supplementary European Search Report dated Mar. 1, 2004; App. No. EP 01 93 9305; 3 pages.

* cited by examiner

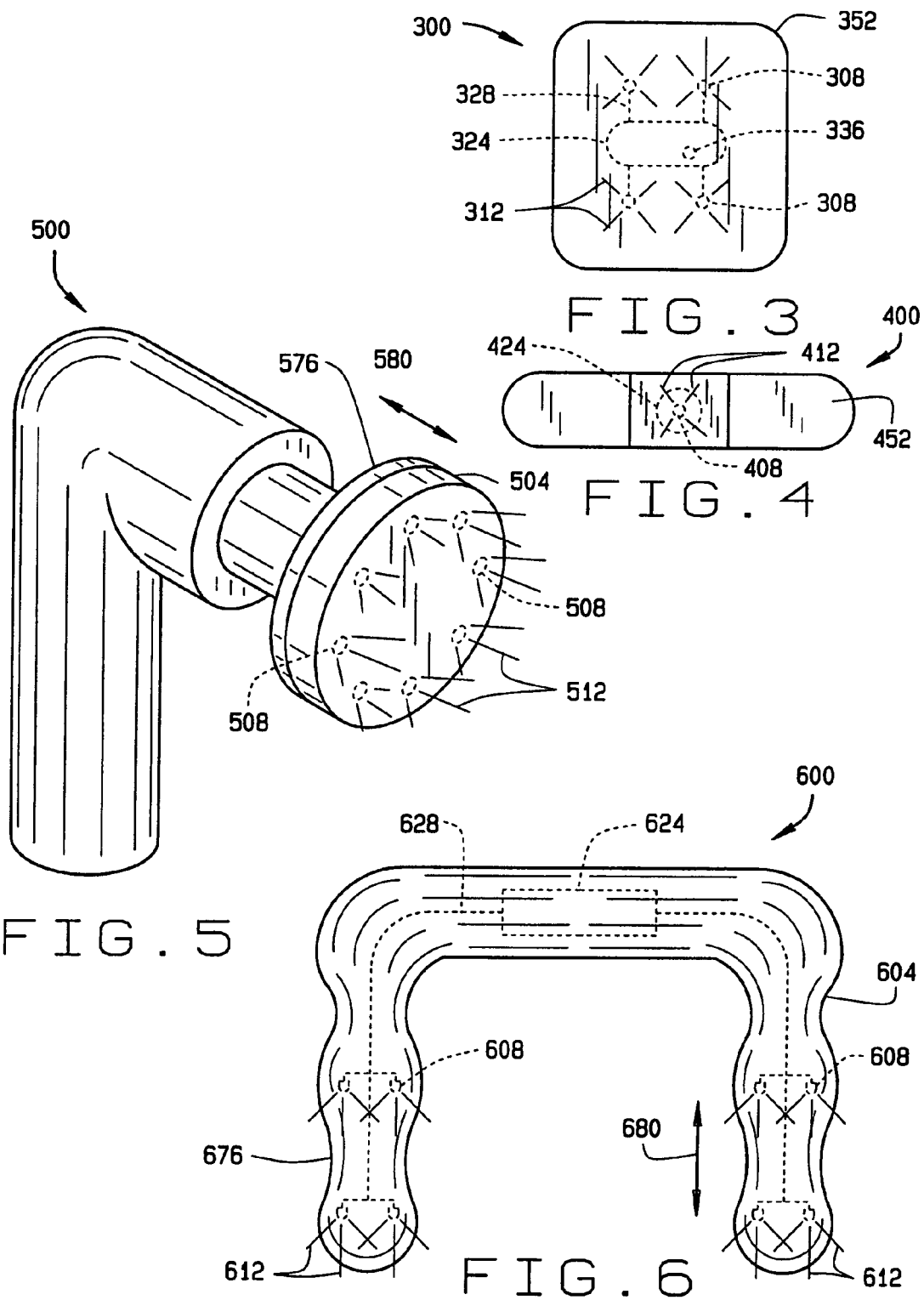

THERAPEUTIC DEVICES AND METHODS FOR APPLYING THERAPY

CROSS-REFERENCE TO RELATED APPLICATION

This application is a continuation-in-part of allowed U.S. patent application Ser. No. 10/786,995 filed Feb. 25, 2004 now U.S. Pat. No. 7,052,167, the contents of which are incorporated herein by reference.

FIELD

The present invention relates generally to therapeutic devices and methods, and more particularly (but not exclusively) to therapeutic devices and methods for applying phototherapy or therapeutic light.

BACKGROUND

The statements in this section merely provide background information related to the present disclosure and may not constitute prior art.

Every day people incur injuries and ailments to various parts of their bodies, and seek therapy from a number of sources including doctors, physical therapists, masseuses, and/or by using at-home therapeutic devices. This therapy is often designed to relieve pain associated with the ailment and/or to encourage more rapid healing to speed up recovery and allow the injured person to return more quickly to normal life.

SUMMARY

According to various aspects, exemplary embodiments are provided of therapeutic devices and methods for applying therapy. In various embodiments, a therapeutic device generally includes one or more light sources for emitting therapeutic light. In some embodiments, the therapeutic device can also include means for applying hot therapy and/or cold therapy to a user's body when the therapeutic device is applied to the user's body. As other examples, various embodiments of therapeutic devices can include massagers and/or adhesive bandage strips for attaching the lighted therapeutic device to the user's body.

In one exemplary embodiment, a therapeutic device generally includes at least one light source for emitting therapeutic light. The therapeutic device also includes a hot/cold gel pack configured in a generally annular shape having a central opening. The central opening is sized to frictionally receive the member having the at least one light source so as to form an interference fit therewith.

In another exemplary embodiment, a therapeutic device generally includes a first container and a second container within the first container. First and second agents are within the respective first and second containers. When the second container is broken, the first and second agents can chemically react to produce chemiluminescent therapeutic light for applying phototherapy to a user's body.

In another exemplary embodiment, a therapeutic device generally includes a massager for applying massage therapy to a user's body. The therapeutic device also includes at least one light source for emitting therapeutic light for applying phototherapy to the user's body. The therapeutic device further includes at least a portion having a non-ambient temperature for applying hot or cold therapy to the user's body. The massager, the at least one light source, and the non-ambient portion are disposed relative to one another such that the therapeutic device can substantially simultaneously apply phototherapy, massage therapy, and hot or cold therapy to the user's body.

In another exemplary embodiment, a therapeutic device generally includes a container having a pocket on an outer surface of the container. A non-electrical agent is within the container for applying at least one of hot therapy and cold therapy. The therapeutic device also includes a member having at least one light source for emitting therapeutic light. The member is sized to be positioned within the pocket. The therapeutic device further includes a massager coupled to the container.

In another exemplary embodiment, a therapeutic device generally includes a container having a pocket on an outer surface of the container and at least one flexible portion. A non-electrical agent is within the container for applying at least one of hot therapy and cold therapy. The therapeutic device also includes a member sized to be positioned within the pocket. The member includes at least one light source for emitting therapeutic light. At least one switching device is positioned internally relative to the container's flexible portion when the member is positioned within the pocket such that movement of the container's flexible portion switchably connects the at least one light source to at least one power source.

In another exemplary embodiment, a therapeutic device generally includes a relatively thin substrate, at least one light source for emitting therapeutic light coupled to the substrate, and a hot/cold gel pack. The therapeutic device also includes an adhesive bandage strip for attaching the device to a user's body with the at least one light source directed to emit therapeutic light generally towards the user's body and with the hot/cold gel pack positioned to apply hot or cold therapy to the user's body. At least one conductive lead is coupled to the substrate and electrically connects the at least one light source to at least one power source. At least one switching device is coupled to the substrate for switchably connecting the at least one light source to the at least one power source. The substrate and the hot/cold gel pack have sufficient flexibility for allowing the therapeutic device to be bent in conformance with a contoured portion of a user's body.

In another exemplary embodiment, a therapeutic device generally includes a container having a pocket on an outer surface of the container. A non-electrical agent is within the container for applying at least one of hot therapy and cold therapy. The therapeutic device also includes a member having at least one light source for emitting therapeutic light. The member is sized to be removably positioned within the pocket. At least one conductive lead electrically connects the at least one light source to at least one power source. At least one switching device is coupled to the substrate for switchably connecting the at least one light source to the at least one power source.

In another exemplary embodiment, a therapeutic device generally includes a container having a pocket on an outer surface of the container. The therapeutic device also includes at least one light source for emitting therapeutic light for applying phototherapy to a user's body, and a hot/cold gel pack for applying hot or cold therapy to the user's body. One of the hot/cold gel pack or the at least one light source is sealed within the container, and the other is removably positioned within the pocket.

Other aspects of the present disclosure relate to methods of applying therapy with a therapeutic device. Some exemplary methods may include using a therapeutic device that has one or more light sources capable of emitting therapeutic light.

The therapeutic device may also include a massager. In one exemplary embodiment, a method generally includes applying the therapeutic device to a user's body for applying at least one of phototherapy and massage therapy to the user's body.

Further aspects and features of the present disclosure will become apparent from the detailed description provided hereinafter. In addition, any one or more aspects of the present disclosure may be implemented individually or in any combination with any one or more of the other aspects of the present disclosure. It should be understood that the detailed description and specific examples, while indicating exemplary embodiments of the present disclosure, are intended for purposes of illustration only and are not intended to limit the scope of the present disclosure.

DRAWINGS

The drawings described herein are for illustration purposes only and are not intended to limit the scope of the present disclosure in any way.

FIG. 3 illustrates a therapeutic device according to another exemplary embodiment of the invention;

FIG. 4 illustrates a therapeutic device according to another exemplary embodiment of the invention;

FIG. 5 is a perspective view of a therapeutic device according to another exemplary embodiment of the invention;

FIG. 6 illustrates a therapeutic device according to another exemplary embodiment of the invention;

DETAILED DESCRIPTION

Figure 1:
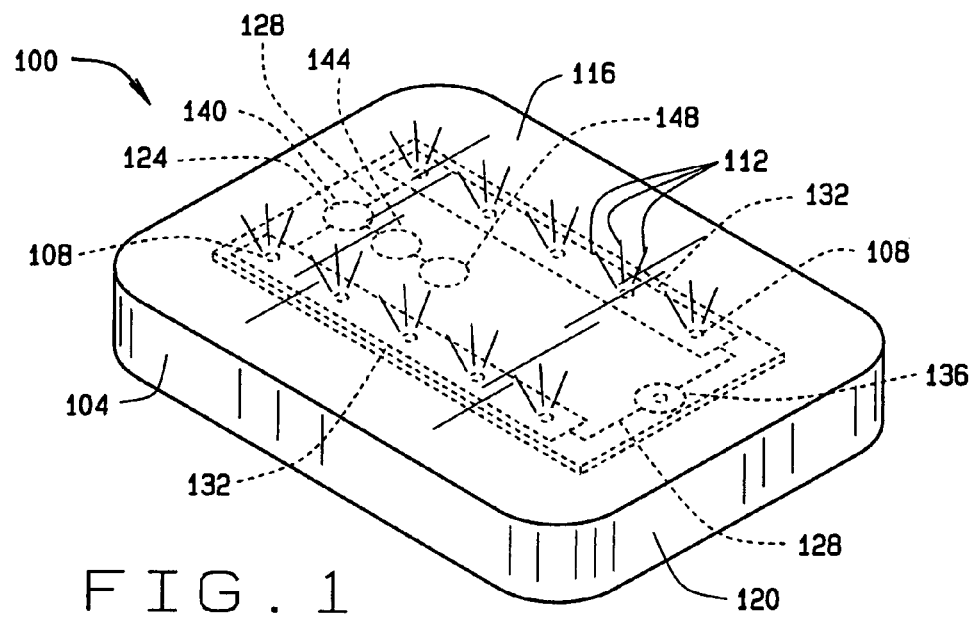
FIG. 1 is a perspective view of a therapeutic device according to an exemplary embodiment of the invention.

The following description is merely exemplary in nature and is not intended to limit the present disclosure, application, or uses.

According to various aspects, exemplary embodiments are provided of therapeutic devices and methods for applying therapy. In various embodiments, a therapeutic device generally includes one or more light sources for emitting therapeutic light. In some embodiments, the therapeutic device can also include means for applying hot therapy and/or cold therapy to a user's body when the therapeutic device is applied to the user's body. As other examples, various embodiments of therapeutic devices can include massagers and/or adhesive bandage strips for attaching the lighted therapeutic device to the user's body.

Exemplary light sources include LEDs (and other lights) capable of emitting colored light. Other exemplary light sources include LEDs (and other lights) capable of emitting infrared light or near infrared light having a wavelength within a range of about 680 nanometers and about 880 nanometers. In an exemplary embodiment, a therapeutic device can include a plurality of LEDs capable of producing therapeutic light at 680 nanometers, 730 nanometers, and/or 880 nanometers. In another exemplary embodiment, a therapeutic device can include a single LED capable of simultaneously producing therapeutic light at 680 nanometers, 730 nanometers, and 880 nanometers. In another exemplary embodiment, a therapeutic device can include a single LED capable of being preset or preprogrammed (e.g., in accordance with the user's input) for producing therapeutic light having a particular wavelength (e.g., 680 nanometers, 730 nanometers, 880 nanometers, etc.) for a certain length of time. After expiration of that certain length of time, the LED may then produce light having a different wavelength for a length of time, which, again, may be in accordance with a user's input. In another exemplary embodiment, a therapeutic device can include one or more LEDs capable of producing colored light and/or a soothing light display (e.g., light that pulsates or changes fairly slowly between two or more colors, etc.). The colored light and/or soothing light display may, for example, be visibly observed by a user for relaxation and stress relief. By way of example, the therapeutic device may comprise an eye mask having the LEDs that produce colored light having a soothing effect on the wearer of the eye mask.

The therapeutic device can also include means for applying hot therapy and/or cold therapy to a user's body when the therapeutic device is applied to the user's body. The means for applying heat and/or cold therapy can include a wide range of suitable materials bearing cold-retaining and/or heat-retaining properties, such as materials generally used in hot/cold gel packs, reusable ice-packs, reusable heating packs or pads, single-use hand and toe warmers, among other suitable materials.

In addition to, or as an alternative to the means for applying hot/cold therapy, the therapeutic device can include either or both a massager and/or an adhesive bandage strip for attaching the therapeutic device to a user's body.

In one exemplary embodiment, a therapeutic device generally includes at least one light source for emitting therapeutic light. The therapeutic device also includes a hot/cold gel pack configured in a generally annular shape having a central opening. The central opening is sized to frictionally receive the member having the at least one light source so as to form an interference fit therewith. The therapeutic device may also include a massager to which the hot/cold gel pack is removably attached.

In another exemplary embodiment, a therapeutic device generally includes a first container and a second container within the first container. First and second agents are within the respective first and second containers. When the second container is broken, the first and second agents chemically react to produce chemiluminescent therapeutic light, which, in turn, can apply phototherapy to a user's body.

In another exemplary embodiment, a therapeutic device generally includes a massager for applying massage therapy to a user's body. The therapeutic device also includes at least one light source for emitting therapeutic light for applying phototherapy to the user's body. The therapeutic device further includes at least a portion having a non-ambient temperature for applying hot or cold therapy to the user's body. The massager, the at least one light source, and the non-ambient portion are disposed relative to one another such that the therapeutic device can substantially simultaneously apply phototherapy, massage therapy, and hot or cold therapy to the user's body.

In another exemplary embodiment, a therapeutic device generally includes a container having a pocket on an outer surface of the container. A non-electrical agent is within the container for applying at least one of hot therapy and cold therapy. The therapeutic device also includes a member having at least one light source for emitting therapeutic light. The member is sized to be positioned within the pocket. The therapeutic device further includes a massager coupled to the container.

In another exemplary embodiment, a therapeutic device generally includes a container having a pocket on an outer surface of the container and at least one flexible portion. A non-electrical agent is within the container for applying at least one of hot therapy and cold therapy. The therapeutic device also includes a member sized to be positioned within the pocket. The member includes at least one light source for emitting therapeutic light. At least one switching device is positioned internally relative to the container's flexible portion when the member is positioned within the pocket such that movement of the container's flexible portion switchably connects the at least one light source to at least one power source. In some embodiments, the at least one power source may be directly or indirectly mounted to or supported/carried by the member. Alternatively, the at least one power source may be spaced apart or be remote from the therapeutic device. In such alternative embodiments, at least one remote power source (e.g., rechargeable battery pack, wall outlet, etc.) can provide the electrical power for operation of the light source(s), which, in turn, may be electrically connected to the remote power source by electrical wiring or a cord (e.g., an insulated flexible electric wire fitted with a plug, etc.). This can also allow for heating and/or cooling of the non-electrical agent without also having to heat or cool the power source(s).

In another exemplary embodiment, a therapeutic device generally includes a relatively thin substrate, at least one light source for emitting therapeutic light coupled to the substrate. For example, the at least one light source may be directly or indirectly supported/carried by the substrate. The at least one light source may also be directly attached, affixed, or mounted to (e.g., surface mounted, etc.) or indirectly mounted to the substrate. Continuing with this embodiment, the therapeutic device also includes a hot/cold gel pack. The therapeutic device further includes an adhesive bandage strip for attaching the device to a user's body with the at least one light source directed to emit therapeutic light generally towards the user's body and with the hot/cold gel pack positioned to apply hot or cold therapy to the user's body. At least one conductive lead is coupled (e.g., directly or indirectly carried or supported by, attached, mounted, affixed, etc.) to the substrate and electrically connects the at least one light source to at least one power source. At least one switching device is coupled (e.g., directly or indirectly carried or supported by, attached, mounted, affixed, etc.) to the substrate for switchably connecting the at least one light source to the at least one power source. The substrate and the hot/cold gel pack preferably have sufficient flexibility for allowing the therapeutic device to be bent in conformance with a contoured portion of a user's body. In some embodiments, the at least one power source may be directly or indirectly supported/carried by or mounted to the member. Alternatively, the at least one power source may be spaced apart or be remote from the therapeutic device. In such alternative embodiments, at least one remote power source (e.g., rechargeable battery pack, wall outlet, etc.) can provide the electrical power for operation of the light source(s), which, in turn, may be electrically connected to the remote power source by electrical wiring or a cord (e.g., an insulated flexible electric wire fitted with a plug, etc.). This can also allow for heating and/or cooling of the non-electrical agent without also having to heat or cool the power source(s).

In another exemplary embodiment, a therapeutic device generally includes a container having a pocket on an outer surface of the container. A non-electrical agent is within the container for applying at least one of hot therapy and cold therapy. The therapeutic device also includes a member having at least one light source for emitting therapeutic light. The member is sized to be removably positioned within the pocket. At least one conductive lead electrically connects the at least one light source to at least one power source. At least one switching device is coupled (e.g., directly or indirectly carried or supported by, attached, mounted, affixed, etc.) to the substrate for switchably connecting the at least one light source to the at least one power source. In some embodiments, the at least one power source may be directly or indirectly supported/carried by or mounted to the member. Alternatively, the at least one power source may be spaced apart or be remote from the therapeutic device. In such alternative embodiments, at least one remote power source (e.g., rechargeable battery pack, wall outlet, etc.) can provide the electrical power for operation of the light source(s), which, in turn, may be electrically connected to the remote power source by electrical wiring or a cord (e.g., an insulated flexible electric wire fitted with a plug, etc.). This can also allow for heating and/or cooling of the non-electrical agent without also having to heat or cool the power source(s).

In other embodiments, the therapeutic device generally includes a container having a pocket on an outer surface of the container. The therapeutic device also includes one or more light source for emitting therapeutic light within the container. The therapeutic device further includes a hot/cold gel pack removably positioned within the pocket. In some embodiments, the therapeutic device also includes a massager.

Other aspects relate to methods of applying therapy with a therapeutic device. Some exemplary methods may include using a therapeutic device that has one or more light sources capable of emitting therapeutic light. The therapeutic device may also include at least a non-ambient portion having a temperature greater or less than ambient temperature. In an exemplary embodiment, a method generally includes applying the non-ambient portion to a user's body with the light source directed to emit therapeutic light toward the user's body. Accordingly, the therapeutic device can apply heat or cold therapy and/or phototherapy to the user's body.

Other exemplary methods may include using a therapeutic device that has a massager and one or more light sources capable of emitting therapeutic light. In one exemplary embodiment, a method generally includes applying the therapeutic device to a user's body for applying at least one of phototherapy and massage therapy to the user's body.

Various embodiments can advantageously allow for application of one or more types of therapy (e.g., phototherapy, heat therapy, cold therapy, massage therapy, combinations thereof, etc.) to a user's body. Various embodiments can enable two or more different types of therapy to be applied to a user's body generally simultaneously. Yet other embodiments can enable different types of therapy to be applied at different times, for example, in a predetermined sequence, alternating pattern, etc. Any of the various aspects of the present invention disclosed herein can be used individually or in combination with any one or more of the other aspects.

FIG. 1 illustrates an exemplary therapeutic device 100 embodying one or more aspects of the present disclosure. As shown in FIG. 1, the therapeutic device 100 includes a container 104. The device 100 also includes one or more light sources 108 for emitting therapeutic light 112 and means, within the container 104, for applying heat therapy and/or cold therapy to a user's body.

The container 104 can be formed from a wide range of materials. Exemplary materials include polymers, plastics, flexible materials, rigid materials, materials capable of being mass produced with relatively low manufacturing costs, among others.

In the exemplary embodiment shown in FIG. 1, the light sources 108 are shown within the container 104 directing therapeutic light 112 through the container surface 116. The container surface 116 is formed of a light-transmissive material that allows the light 112 to pass therethrough. Alternatively, the container surface 116 may be opaque and provided with openings or holes to allow the light 112 to escape or pass through the holes for application to a user's body.

In addition, exemplary embodiments can include a container 104, or at least portions thereof, which are sufficiently flexible or bendable to allow the device 100 to be conformed or contoured to a portion of a user's body. By way of example, the container 104 can be formed from a material having sufficient elasticity or flexibility to be wrapped at least partially around a particular portion of a user's body (e.g., arm (FIG. 10), leg, finger, etc.). Alternatively, the container, or at least a portion thereof, can be formed from a relatively rigid material.

The container 104 can be provided in a wide range of shapes and colors. In the illustrated embodiment, the container 104 is generally rectangular. Alternatively, other embodiments include containers in various other geometric shapes, fanciful shapes, recognizable and well-known shapes. Exemplary container shapes include spherical, circular, semicircular, triangular, diamond shaped, discs, cubes, prisms, mouse head, star, fish, dinosaur, food item, hearts, football, among others. The particular shape of a container can be determined at least in part by user preference, which, in turn, can be based on any number of factors including the user's interests and age.

Further, the container 104, and also the device 100, can be provided in various sizes. In a preferred embodiment, the container 104 is relatively compact so that the device 100 is readily portable. The size of the therapeutic device 100 and its container 104 can depend, at least in part, on the particular size of the ailment or body portion to which the therapeutic device 100 is to be applied.

In various embodiments, the container 104 can be at least partially hollow and define an internal cavity. The cavity of the container 104 can be filled (or at least partially filled) with any of a wide range of agents or substances bearing cold-retaining and/or heat-retaining properties such as materials generally used in hot/cold gels, reusable ice-packs, reusable heating pads, single use hand warmers, refreezable liquids or semi-liquids, reheatable liquids or semi-liquids, Insul-Ice reusable ice available from PCM Thermal Solutions, Inc. of Naperville, Ill., among other suitable materials.

By way of example, the container 104 can include a filler adapted to retain heat for an extended or prolonged period of time (e.g., 20 minutes, 30 minutes, etc.) after the filler has been heated, for example, by heating the container 104 in a conventional oven, microwave, hot water, etc. The filler can also, or alternatively, be adapted to retain cold for an extended or prolonged period of time (e.g., 20 minutes, 30 minutes, etc.) after the filler has been cooled, for example, by placing the container within a freezer, etc. By way of example only, the filler may comprise a refreezable, reusable, non-toxic liquid gel coolant, which is hermetically sealed in the container 104.

In other embodiments, the container 104 itself can be formed or manufactured from a material capable of maintaining cold or heat. In yet other embodiments, the therapeutic device 100 can include means for self-generating heat and/or cold. For example, the device 100 can include any of a wide range of substances that begin to activate and generate their own heat or cold when exposed to air, such as materials generally used in commercially available hand and toe warmers. In such embodiments, the device 100 can be vacuum sealed within a suitable package, and can begin generating heat or cold (as the case may be) when the package is opened thereby exposing the device to air.

In further embodiments, the therapeutic device 100 can include a material generally used in instant single-use cold compresses (e.g., ammonium nitrate and water, etc.) and/or instant single-use hot compresses (e.g., calcium chloride and water, etc.). In such embodiments, the container 104 can be activated to generate heat or cold by shaking the contents of the container 104 and/or squeezing the container 104 to cause a chemical reaction or phase change of the material(s) within the container 104.

The light sources 108 will now be described in more detail. The light sources 108 can include a plurality of LEDs capable of emitting therapeutic light. In some implementations, the therapeutic light can provide energy stimulation to human tissue to increase cellular activity during the healing process.

The LEDs 108 can be capable of emitting infrared light, near infrared light, and/or light having a wavelength within a range of about 680 nanometers and about 880 nanometers. Alternatively, other suitable light sources capable of emitting therapeutic light may be employed. Exemplary light sources include other LEDs, laser, chemiluminescent light sources (e.g., glow sticks, etc.), electroluminescent light sources, bioluminescent light sources, and the like.

The particular type of light source(s) can depend, at least in part, on the particularities of the ailment for which the therapeutic device is to be used. The selection of light source can also depend, at least in part, on size and weight restrictions (if any), in which case LEDs may be selected because LEDs are typically compact, lightweight, and do not generate excessive amounts of heat during operation.

Optionally, one or more of the LEDs 108 may produce other forms of light besides infrared or near infrared therapeutic light. By way of example only, one or more LEDs 108 may produce colored light, which may also have a therapeutic soothing or relaxing effect.

As shown in FIG. 1, each LED 108 is positioned within the container 104. The LEDs 108 are oriented to direct light 112 through the container surface 116. Alternatively, each LED 108 need not be positioned entirely within the container 104. Instead, one or more of the LEDs 108 may be partially or entirely positioned external to the container 104, for example, on the container surface 116. Further, each LED 108 need not be positioned to direct light through the container surface 116. Instead, one or more of the LEDs 108 can be oriented to direct light through the container's sidewalls 120 and/or bottom surface.

In the exemplary embodiment of FIG. 1, the LEDs 108 are arranged in two generally parallel rows of five LEDs 108. Alternatively, other embodiments can include any suitable number of (i.e., one or more) LEDs in various other arrangements and arrays (e.g., large flat arrays, small arrays, circular arrays (FIG. 5), semicircular arrays, triangular arrays, zigzagging arrays, etc.). The number and arrangement of LEDs can depend, at least in part, on the type and size of ailment for which the therapeutic device is to be used. The number and arrangement of LEDs can also depend, at least in part, on size and weight restrictions (if any) placed on the therapeutic device. For example, various embodiments can include therapeutic devices that are relatively small, lightweight, and thus suitable for use by lightly equipped, highly mobile special operations troops. Because wounds can pose serious physical risk during combat operations, lightweight therapeutic devices that promote wound healing and musculoskeletal rehabilitation and conditioning can be advantageous.

As shown in FIG. 1, the LEDs 108 are interconnected to a power source 124 by conductive leads or paths 128. In the illustrated embodiment, the light sources 108 and portions of the conductive leads 128 are surface mounted on (e.g., electronically welded onto, etc.) a flexible lightweight ribbon cable 132, although other conductive leads and mounting methods are also possible.

The operation of the light sources 108 may be controlled by at least one switch 136. The switch 136 may, for example, allow the user to select from among various display modes for the light sources 108, such as an off-light mode, an on-light mode, a mode in which the light sources 108 emit steady or non-flashing light, a mode in which the light sources 108 emit light intermittently, a mode in which the light sources 108 blink at different times in accordance with a predetermined sequence or order, a mode in which the light sources 108 emit light that phases between or blends colors, a mode in which the light sources 108 emit light randomly, and/or a mode in which the light sources 108 pulsate to sounds.

In the illustrated embodiment, the switching device 136 is a push button switch for switchably connecting the light sources 108 to the power source 124. As shown, the switch 136 is positioned within the container 104. The switch 136 can be coupled to an externally flexible surface portion 116 of the container 104 such that application of external pressure upon the externally flexible surface portion 116 activates the switch 136 thereby causing operation of the light sources 108. The external pressure may, for example, be applied by the user squeezing the container 104 at the externally flexible surface portion 116. The switch 136 may also allow the user to cycle through the various display modes or select a particular type of light (e.g., therapeutic light, colored light, etc.) to be emitted by the light sources 108 by successively squeezing the container 104 at about the externally flexible surface portion 116. Additionally, the switch 136 may also allow the user to dim or brighten the intensity of the light, for example, by holding down the switch 136 with continuously applied pressure to the container 104 at about the externally flexible surface portion 116.

Alternatively, the switch 136 may include one or more other suitable switching devices or means including electrical terminals for switchably connecting the light sources to the power source when the electrical terminals are placed in contact with the user's body, motion-responsive switches, light-sensitive switches, temperature-sensitive switches, compression switches, voice activated switches, etc. For example, the switch may be a light-sensitive switch such that the light sources are activated when the ambient light level falls below a predetermined threshold.

In the illustrated embodiment of FIG. 1, the power source 124 comprises three watch batteries 140, 144, and 148 electrically connected in series. Alternatively, the power source 124 may be any suitable means of providing energy to the light sources 108 including renewable batteries, rechargeable batteries, disposable batteries, solar cells, and other suitable power sources, including kinetic power sources.

A therapeutic device can, but need not necessarily, include an attachment device for attaching the therapeutic device to a user. By way of example only, FIG. 3 illustrates a therapeutic device 300 that includes an adhesive patch 352, and FIG. 4 illustrates a therapeutic device 400 that includes an adhesive bandage strip 452, as described in more detail below.

Figure 8:
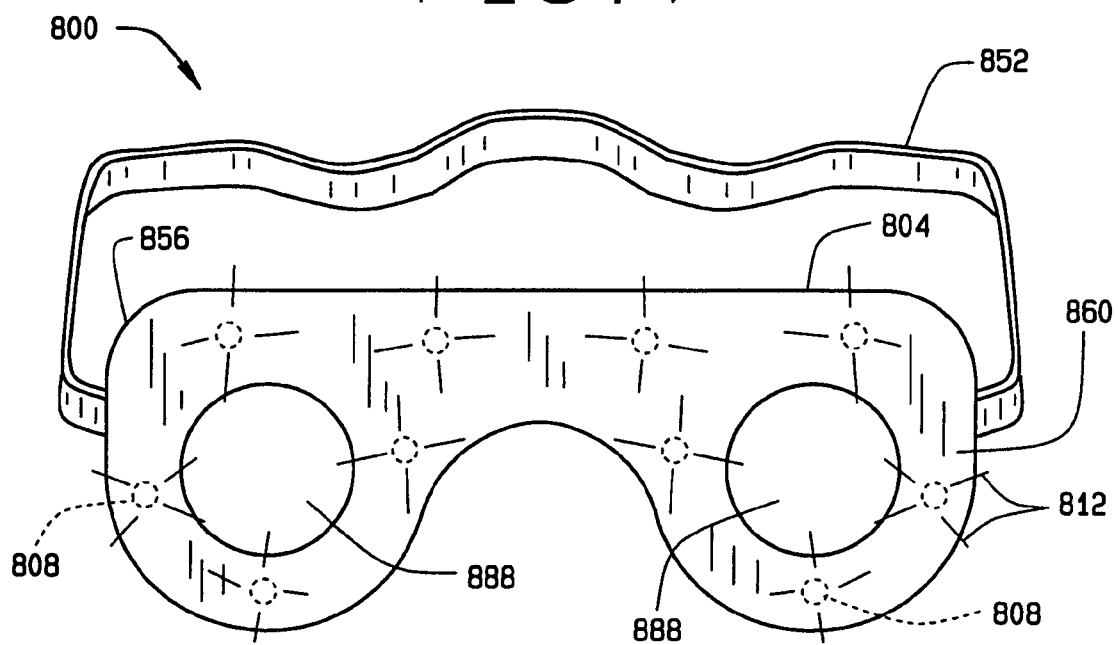
FIG. 8 is a perspective view of a therapeutic device according to another exemplary embodiment of the invention.

An attachment device of the therapeutic device 800 in FIG. 8 includes an elastic band 852 attached to opposed ends 856 and 860 of the container 804. The elastic band 852 can have a sufficient length and/or elasticity to allow the elastic band 852 and container or eye mask 804 to be disposed around the user's head, thereby attaching the therapeutic device 800 to the user's head.

Or for example, a therapeutic device can be adapted to enable the device to be disposed generally around a portion of the user's body (shoulder, knee, back, arm, etc.), with the ends being secured to one another via a suitable attachment mechanism, such as hook and loop closures, adhesives, neoprene material connecting the two opposed ends, etc.

Figure 10:
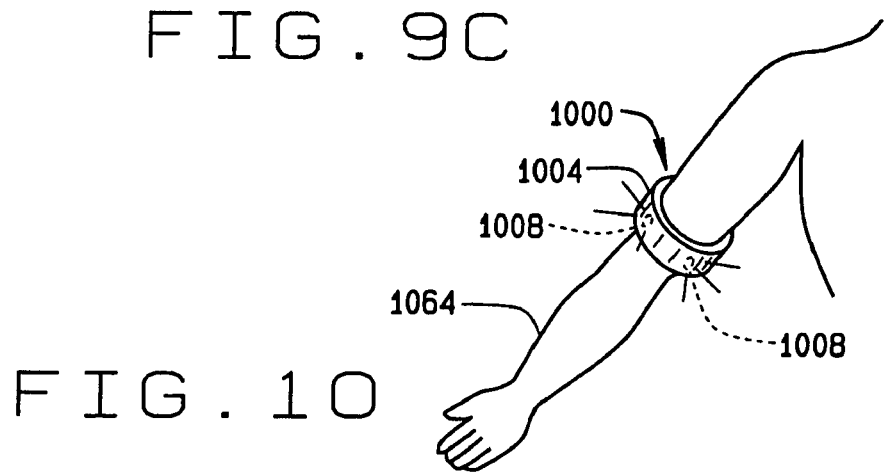
FIG. 10 is a perspective view of a therapeutic device according to another exemplary embodiment of the invention.

In yet other embodiments, however, the therapeutic device need not include a separate attachment device. For example, FIG. 10 illustrates a therapeutic device 1000 including a container 1004 having a sufficient size and/or elasticity to be disposed and/or stretched around a user's arm 1064 preferably in a manner that resists unintentional loosening or detachment of the therapeutic device 1000 from the user but that also permits easy removal of the device 1000 from the user. The therapeutic device 1000 also includes one or more light sources 1008 for emitting therapeutic light, and means within the container 1004 for applying heat and/or cold therapy. Alternatively, the therapeutic device 1000 can be adapted to be disposed around other portions of the user's body, such as an ankle, shoulder, leg, back, etc. Again, however, other attachment devices may be employed in various embodiments of the invention.

Figure 2:
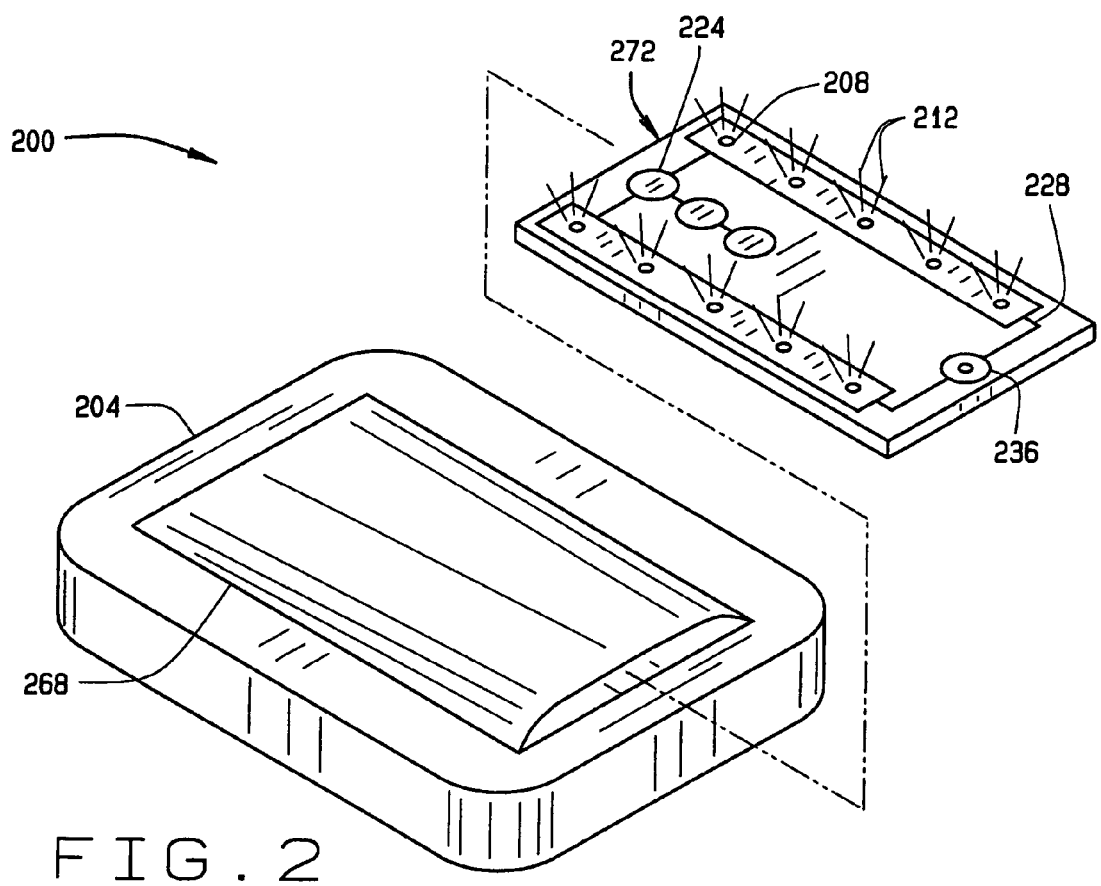
FIG. 2 is a perspective view of a therapeutic device according to another exemplary embodiment of the invention.

FIG. 2 illustrates another embodiment of a therapeutic device 200 including light sources 208 that are removably coupled to a container 204. The light sources 208 are capable of emitting therapeutic light 212. The container 204 can further include means for applying hot/cold therapy, such as a hot/cold gel pack.

As shown in FIG. 2, the container 204 defines a sleeve or pocket 268 sized to receive the apparatus or packet 272 that includes the light sources 208, one or more power sources 224, conductive leads 228, and a switching device 236 for switchably connecting the light sources 208 to the power sources 224 via the conductive leads 228. Alternatively, other suitable methods for removably coupling the light sources 208 to the container 204 can be employed.

By removing the light sources 208 from the container 204, the container 204 can then be stored (e.g., in a freezer, etc.), heated (e.g., heated in a conventional oven, microwave, hot water, etc.), and/or cooled (e.g., refrigerated, etc.) separately from the light sources 208. In other embodiments, the light sources 208 may be positioned (e.g., sealed, hermetically sealed, etc.) within the container 204, and a hot/cold gel pack may be removably positioned within the pocket 268. In such alternative embodiments, the hot/cold gel pack can be removed from the pocket 268 such that the hot/cold gel pack can then be stored (e.g., in a freezer, etc.), heated (e.g., heated in a conventional oven, microwave, hot water, etc.), and/or cooled (e.g., refrigerated, etc.) separately from the light sources 208.

With further reference to FIG. 3, the therapeutic device 300 includes an adhesive patch 352 and one or more light sources 308 for emitting therapeutic light 312 (e.g., infrared light having healing properties associated therewith, other light having therapeutic effect, etc.). The light sources 308 can be positioned relative to the adhesive portion 352 such that the light sources 308 emit therapeutic light 312 generally toward the user's body when the device 300 is attached to the user 300 via the adhesive portion 352.

As shown, the device 300 includes a power source 324, conductive leads 328 and a switching device 336 (e.g., push button switch, etc.) for switchably connecting the light sources 308 to the power source 324 via the conductive leads 328.

The therapeutic device 300 can also include means for applying hot and/or cold therapy to the user's body. For example, the therapeutic device 300 can include a hot/cold gel pack coupled to the adhesive patch 352.

Further, the therapeutic device 300 can be provided in various shapes and sizes. For example, the shape, height, and width of the adhesive patch 352 can depend, at least in part, on the particular size of the ailment or body portion to which the therapeutic device 300 is to be applied.

FIG. 4 illustrates a therapeutic device 400 that includes an adhesive bandage strip 452 and one or more light sources 408 for emitting therapeutic light 412. The light sources 408 can be positioned relative to the adhesive portion 452 of the device 400 such that the light sources 408 emit therapeutic light 412 generally toward the user's body when the device 400 is attached to the user 400 via the adhesive portion 452. As shown, the device 400 includes a power source 424 for powering a single LED 408, although other suitable quantities of light sources can also be employed in device 400.

The therapeutic device 400 can also include means for applying hot and/or cold therapy to the user's body. By way of example, the therapeutic device 400 can include a hot/cold gel pack coupled to the adhesive portion 452.

Further, the therapeutic device 400 can be provided in various sizes. For example, the length and width of the adhesive bandage strip 452 can depend, at least in part, on the particular size of the ailment or body portion to which the therapeutic device 400 is to be applied.

FIGS. 5 and 6 illustrates exemplary embodiments of therapeutic devices 500 and 600, each respectively including one or more light sources 508, 608 for emitting therapeutic light 512, 612 and a massager 576, 676. As shown, the light sources 508, 608 can be positioned to direct therapeutic light 512, 612 generally toward a user's body when the massager 576, 676 is applying massage therapy (as represented by arrows 580, 680) to a portion of the user's body, for example, to relieve sore muscles, etc. Accordingly, the therapeutic devices 500 and 600 can apply massage therapy and/or therapeutic light to a user's body generally simultaneously or at different times.

The devices 500 and/or 600 can, but need not include means for applying heat therapy and/or cold therapy. In such embodiments, the devices 500 and/or 600 can apply hot/cold therapy, massage therapy, and/or therapeutic light to a user's body generally simultaneously or at different times.

By way of example only, the devices 500 and 600 can each include a container 504, 604 in which is positioned a hot/cold gel or other suitable substance. The container 504 can be removable from the device 500. Each container 504, 604 can also include one or light-transmissive surfaces (e.g., acrylic, etc.) to allow therapeutic light to pass therethrough.

FIG. 6 further illustrates conductive leads 628 connecting the light sources 608 to a power source 624.

Figure 7:
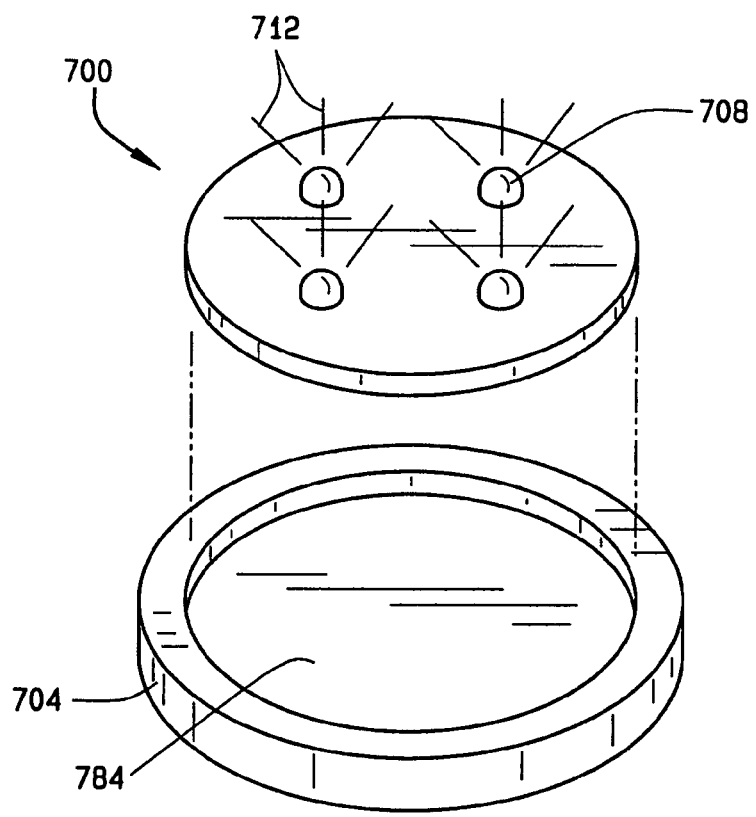
FIG. 7 is a perspective view of a therapeutic device according to another exemplary embodiment of the invention.

FIG. 7 illustrates another embodiment of a therapeutic device 700 including light sources 708 for emitting therapeutic light 712. As shown, the light sources 708 can removably coupled to a hot/cold gel pack 704. The gel pack 704 includes an annular shape (e.g., ring shaped, etc.) having a central opening 784. The central opening 784 is preferably sized to frictionally receive the portion including the light sources 708 so as to form an interference fit therewith. Alternatively, the removable light source portion can be engaged with the gel pack 704 using other suitable fastening systems or methods, such as a threaded connection, resilient ribs, among others.

FIG. 8 illustrates another therapeutic device 800 which includes a container 804. As shown, the device 800 includes a suitable attachment device (e.g., an elastic band 852, etc.) for attaching the device 800 to a user's head. The device 800 can include one or more light sources 808 for emitting therapeutic light 812 (e.g., infrared light, colored light, soothing light, etc.). The device 800 also include means, within or attached to the container 804, for applying hot and/or cold therapy to the facial area adjacent the user's eyes, for example, to relieve or soothe a sinus headache, reduce swelling around the user's eye(s), among other therapeutic purposes. The container 804 also includes eye holes 888 to allow the user to see when wearing the therapeutic device 800.

Figure 9A:
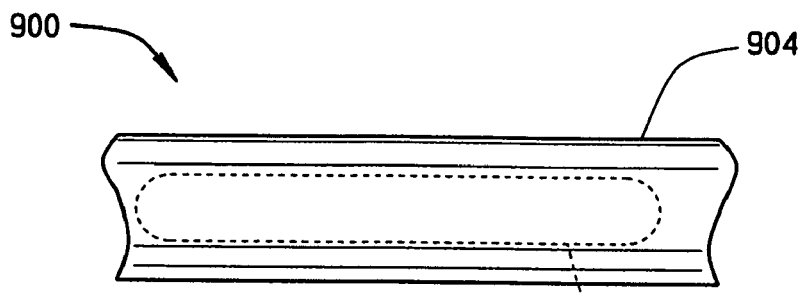
FIGS. 9A through 9C illustrates various stages for activating a light source of a therapeutic device according to another exemplary embodiment of the invention.
Figure 9B:
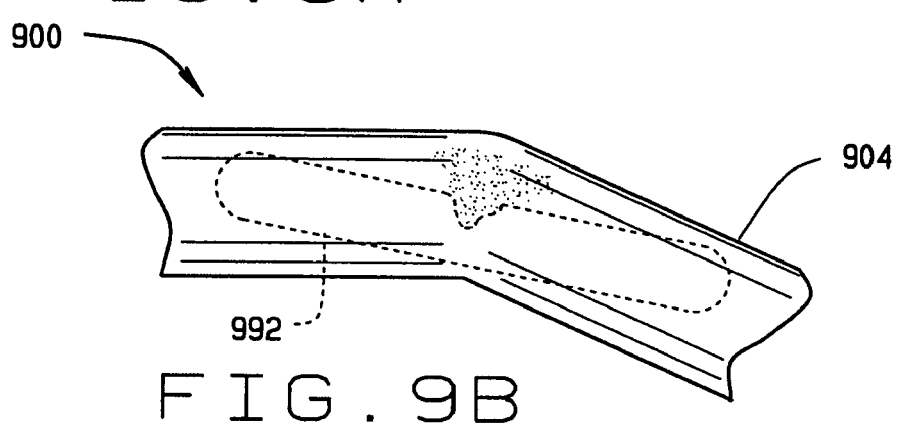

FIGS. 9A through 9B illustrate a therapeutic device 900 that employs chemiluminescence to apply therapeutic light 912 to a user's body. The therapeutic device 900 includes two or more agents or chemical solutions that emit therapeutic light 912 when combined. The solutions can be maintained in separate chambers within the container 904, that is, at least until the therapeutic light 912 is to be applied to the user's body.

Figure 9C:
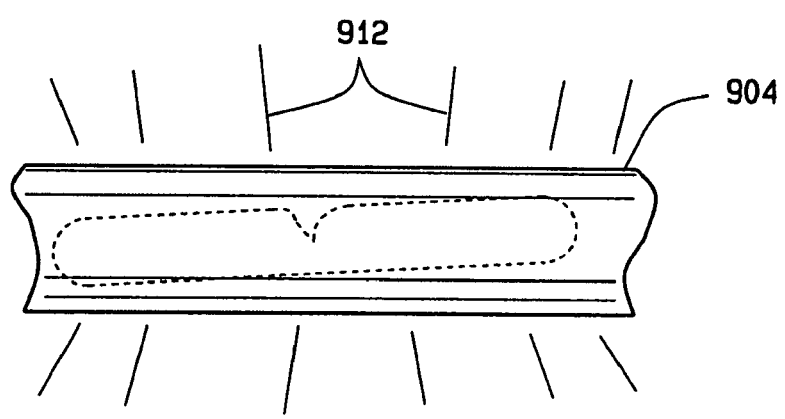

A first chemical solution or activator can be contained within a readily breakable container 992 (e.g., a glass vial, etc.) which, in turn, is inside an outer container 904. The outer container 904 includes another chemical solution. Sufficiently bending the container 904 (FIG. 9B) breaks the breakable container 992, thereby allowing the two solutions to flow together resulting in a chemical reaction that produces therapeutic light 912 (FIG. 9C).

Exemplary chemical agents that can be used with the therapeutic device 900 include an oxalic-type ester in one of the containers 904 and 992, and a hydroperoxide with a solvent and flourescent compound in the other container 904 or 992. The therapeutic device 900 can include a wide range of two part combinations of flourescing agents, which preferably are relatively efficient at producing light over an extended period of time, biodegradable, and/or safe for the environment.

The device 900 can also include means for applying hot/cold therapy. For example, the device 900 can include any of a wide range of agents or substances that begin to activate and self-generate heat or cold when exposed to air. Exemplary materials include those ingredients generally used in hand and toe warmers. For example, the device 900 can include a mixture of various ingredients including iron, charcoal, water, salt, wood fiber, and vermiculite, among other suitable combinations. When exposed to the air, these ingredients can combine and react such that an oxidation process takes place producing heat. In such embodiments, the device 900 can be vacuum sealed within a suitable package that must be opened to expose the device 900 to air. Accordingly, the device 900 can thus be made to apply both therapeutic light and hot/cold therapy (as the case may be) to the user's body by bending the container 904 to crack open the internal breakable container 992, and by opening the package to expose the device 900 to air.

In another embodiment, the device 900 can include a hot/cold gel within the container 904. In which case, the device 900 can apply both therapeutic light and hot/cold therapy to the user's body by heating or cooling the device 900 to a non-ambient temperature (i.e., a temperature more or less than ambient temperature), and bending the container 904 to crack or break open the internal container 992.

In various embodiments, a therapeutic device can include an outer container in which is positioned a filler material (e.g., a hot/cold gel or agent, etc.) and a substantially fluid-tight inner container within the outer container. At least one light source for emitting therapeutic light, at least one power source for powering the light source, and a switching device (e.g., push button switch, a dome push switch, a membrane switch, etc.) can be encapsulated or housed within the inner container, preferably in a fluid-tight fashion. The inner container can be suspended within the filler material and/or coupled (e.g., adhered, affixed, mounted, etc.) to an inner surface of the outer container. The outer container can include at least one externally flexible portion coupled to the switching device within the inner container such that movement of the flexible portion activates the switching device to connect the light source(s) to the power source(s). In various embodiments, the entirety of the outer container can be sufficiently flexible such that applying pressure (e.g., squeezing, compressing, etc.) to the outer container compresses the filler material (e.g., hot/cold gel, among other substances, etc.) within the outer container. In response to the compression, the filler material, in turn, can transmit a compression force to the inner container causing the switch to activate to connect the light source(s) to the power source(s). In embodiments in which the filler material is freezable, the inner container may include an internal cavity or gap for enabling the filler material, even when frozen, to transmit a compression force initially applied to the outer container to the inner container for activating the switching device therein.

Various therapeutic devices (e.g., 100, 200, 300, 400, 500, 600, 700, 800, 900, 1000, etc.) can be provided in a wide range of shapes and sizes, which can depend, at least in part, on the particular ailment or body portion to which the therapeutic device is to be applied.

Various embodiments can also include therapeutic devices defining one or more external and/or internal indicia. The indicia can include a wide range of graphic images, graphic elements, designs, artwork, distinctive marks, identifying symbols, company logos, alphanumeric characters, advertisements, trademarks, sports team insignias, names, monograms, among others. The indicia can be positioned relative to the light sources such that the light sources direct light at the indicia to highlight (e.g., illuminate, backlight, etc.) the indicia. Such indicia can impart holiday themes, professional themes, promotional themes, sports related themes, and the like. Indeed, any suitable theme may be employed and are not limited to these types of themes described above.

Optionally, various embodiments can include a plurality of light-altering particles (e.g., glitter, reflective particles, refractive particles, translucent particles, glass-like prisms, colored particles, clear particles, etc.) within the container (e.g., suspended within the hot/cold gel or other suitable substance within the container). These particles can receive and alter the light from at least one of the light sources to create yet an additional feature. For example, the altered light can produce a visibly pleasing or sparkling light effect. Indeed, various embodiments can produce such visibly pleasing light effects that a user may simply choose to use the device for novelty or display purposes rather than for therapeutic purposes.

Another aspect of the invention provides a method of applying therapy with a therapeutic device. The therapeutic device includes one or more light sources capable of emitting therapeutic light and also includes at least a non-ambient portion having a temperature greater or less than ambient temperature. In an exemplary implementation, the method generally includes applying the non-ambient portion to a user's body with the light source directed to emit therapeutic light toward the user's body. The therapeutic device can then be used to apply heat or cold therapy and/or therapeutic light to the user's body.

The method can also include heating or cooling the therapeutic device prior to applying the non-ambient portion to the user's body. The therapeutic device can also include an attachment device which is used to attach the therapeutic device to the user's body.

The therapeutic device can also include a massager. In which case, the method can further include using the therapeutic device to, generally simultaneously or at different times, apply heat/cold therapy, massage therapy, and/or therapeutic light to the user's body.

Accordingly, various implementations advantageously allow for ready application of one or more types of therapy (e.g., light, heat, cold, massage, a combination thereof, etc.) to a user's body. Various implementations enable two or more types of therapy to be applied to a user's body generally simultaneously. Yet other implementations enable different types of therapy to be applied at different times, for example, in a predetermined sequence, alternating pattern, etc.

Various embodiments can include therapeutic devices capable of being used repeatedly for applying hot therapy, cold thereapy, therapeutic light, massage therapy, and/or combinations thereof. Yet other embodiments can include single-use, disposable therapeutic devices. Various embodiments of a therapeutic device can also be configured to be neutrally buoyant, positively buoyant, or negatively buoyant when placed in a liquid.

Various embodiments can also include at least one power source spaced apart or remote from a therapeutic device. In such embodiments, at least one remote power source (e.g., rechargeable battery pack, wall outlet, etc.) can provide the electrical power for operation of the therapeutic light source(s). The light source(s), in turn, may be electrically connected to the at least one remote power source by electrical wiring or cords (e.g., an insulated flexible electric wire fitted with a plug, etc.). This can also allow for heating and/or cooling of the therapeutic device without also having to heat or cool the power source(s).

While some preferred embodiments have been described herein for applying therapy to humans, embodiments of the invention can also be used to apply therapy to animals, such as common house pets like dogs and cats. Accordingly, the specific references to human or user herein should not be construed as limiting the scope of the present invention to only human subjects.

Any one or more of the various embodiments disclosed herein can be used in various applications and settings (e.g., civilian medical care, military combat operations, etc.) where it would be desirable to have improved therapeutic techniques for, among other things, reducing swelling, relieving joint and muscle stiffness, promoting muscle and tissue regeneration after periods of immobility, confinement or surgery, improving burn treatment, improved muscular skeletal rehabilitation, etc.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order or performance. It is also to be understood that additional or alternative steps may be employed.

The description of the disclosure is merely exemplary in nature and, thus, variations that do not depart from the gist of the disclosure are intended to be within the scope of the disclosure. Such variations are not to be regarded as a departure from the spirit and scope of the disclosure.

What is claimed:

1. A therapeutic device comprising a member including at least one light source for emitting therapeutic light, a hot/cold gel pack configured in a generally annular shape having a central opening, the central opening sized to frictionally receive the member having the at least one light source so as to form an interference fit therewith.

2. The therapeutic device of claim 1, further comprising a massager, and wherein the hot/cold gel pack is removably attached to the massager.

3. A therapeutic device comprising a massager for applying massage therapy to a user's body, at least one light source for emitting therapeutic light for applying phototherapy to the user's body, and at least a portion having a non-ambient temperature for applying hot or cold therapy to the user's body, the massager, the at least one light source, and the non-ambient portion disposed relative to one another such that the therapeutic device can substantially simultaneously apply phototherapy, massage therapy, and hot or cold therapy to the user's body, wherein the massager is coupled to the non-ambient portion, and wherein the at least one light source is coupled to the non-ambient portion.

4. The therapeutic device of claim 3, wherein the non-ambient portion comprises a container and an agent within the container for applying hot or cold therapy to the user's body.

5. The therapeutic device of claim 4, wherein the agent comprises a hot/cold gel.

* * * * *